(12) United States Patent
Yan et al.

(10) Patent No.: US 9,523,647 B2
(45) Date of Patent: Dec. 20, 2016

(54) BACKLIGHT INSPECTION EQUIPMENT (71) Applicants: BOE TECHNOLOGY GROUP CO., LTD., Beijing (CN); BOE OPTICAL SCIENCE AND TECHNOLOGY CO., LTD., Suzhou (CN)

(72) Inventors: David Yan, Beijing (CN); Chunlei Cao, Beijing (CN)

(73) Assignees: BOE TECHNOLOGY GROUP CO., LTD., Beijing (CN); BOE OPTICAL SCIENCE AND TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 14/590,358

(22) Filed: Jan. 6, 2015

(65) Prior Publication Data
US 2015/0346111 A1 Dec. 3, 2015

(30) Foreign Application Priority Data

May 29, 2014 (CN) .......................... 2014 1 0235345

(51) Int. Cl.
G01N 21/00 (2006.01)
G01N 21/95 (2006.01)
G01N 21/88 (2006.01)

(52) U.S. Cl.
CPC .......... *G01N 21/95* (2013.01); *G01N 21/8806* (2013.01); *G01N 2021/9513* (2013.01); *G01N 2201/02* (2013.01); *G01N 2201/068* (2013.01)

(58) Field of Classification Search
USPC ..... 356/237.1–237.6, 239.1–239.8, 600–613
See application file for complete search history.

(56) References Cited

U.S. PATENT DOCUMENTS

| 2009/0153849 A1* | 6/2009 | Moriya | G01N 21/21 356/239.2 |
| 2012/0147365 A1* | 6/2012 | Mitsuhashi | G02F 1/1309 356/239.1 |
| 2014/0055603 A1* | 2/2014 | Lin | G01N 21/95 348/126 |

FOREIGN PATENT DOCUMENTS

| CN | 101922997 A | 12/2010 |
| CN | 201845148 U | 5/2011 |

(Continued)

OTHER PUBLICATIONS

First Office Action regarding Chinese application No. 201410235345.5, dated Jan. 25, 2016. Translation provided by Dragon Intellectual Property Law Firm.

(Continued)

*Primary Examiner* — Tri T Ton
(74) *Attorney, Agent, or Firm* — Harness, Dickey & Pierce, P.L.C.

(57) ABSTRACT

The present invention relates to a backlight inspection equipment comprising a carrying platform configured to dispose a backlight to be inspected and an inspection plate movably disposed relative to the carrying platform. The inspection plate moves from a first position to a second position. When the inspection plate is disposed at the first position, a first light emitting region of the backlight to be inspected is exposed and a second light emitting region which is a region other than the first light emitting region is blocked. When the inspection plate is disposed at the second position, a third light emitting region of the backlight to be inspected, which is different from the first light emitting region, is exposed, and a fourth light emitting region which is a region other than third light emitting region is blocked.

17 Claims, 6 Drawing Sheets

(56) References Cited

FOREIGN PATENT DOCUMENTS

| CN | 202362255 U | 8/2012 |
|---|---|---|
| CN | 203502702 U | 3/2014 |
| JP | 2006153844 A | 6/2006 |
| KR | 20020065098 A | 8/2002 |

OTHER PUBLICATIONS

The Status and Trends of Large-size LED Backlight, 1994-2011 China Academic Journal Electronic Publishing House, LED Industry and Standard.
Second Office Action regarding Chinese application No. 201410235345.5, dated Aug. 12, 2016. Translation provided by Dragon Intellectual Property Law Firm.

\* cited by examiner

BACKLIGHT INSPECTION EQUIPMENT

CROSS-REFERENCE TO RELATED APPLICATION

This application claims priority of Chinese Patent Application No. 201410235345.5, filed on May 29, 2014, which is incorporated herein by reference.

TECHNICAL FIELD

The present invention relates to an auxiliary tool for lighting inspection of a backlight having a large dimension, in particular to a backlight inspection equipment.

BACKGROUND

In TFT-LCD industrial chain, BLU (backlight unit), as an important component of this technical field, needs a lighting inspection after the BLU is assembled. For example, Chinese Patent Application No. 201010160663 discloses an auxiliary tool of a backlight lighting inspection and use method of the auxiliary tool. In Chinese Patent Application No. 201010160663, the auxiliary tool is comparatively used for lighting inspection of a backlight having a small dimension.

The lighting inspection for present backlight having a large or middle dimension is mainly dependent on manual inspection. When inspecting the backlight unit, an inspector uses a thumb and a forefinger to make bow-shape, and moves the fingers above the backlight from a top left corner of the backlight in a Z-shape locus. The inspector performs a visual inspection to the backlight by moving the fingers shaped into bow-shape.

In this inspection method for the backlight lighting, the hand of the inspector is in a suspended state during the inspection, and work intensity of the inspection is hard. Thus, it is hard to avoid a contact of the finger with a surface of the backlight and causing an abnormality. Further, the movement of the fingers in the suspended state is performed without a relevant standard line as a reference. A back and forth distance of the finger movement in the suspended state is only subjectively determined by the inspector, and repeated inspection to the same area or inspection miss may frequently occur.

SUMMARY

The present invention is made in view of the above-described technical difficulties, and an object of the present invention is to provide a backlight inspection equipment that reduces an inspection work difficulty and an inspection work intensity and improves operational efficiency of inspection work and inspection rate.

In order to achieve the above-described purposes, the present invention provides a backlight inspection equipment.

The back light inspection equipment according to an embodiment of the present invention includes a carrying platform configured to dispose a backlight to be inspected and an inspection plate movably disposed relative to the carrying platform. When the inspection plate is disposed at a first position, a first light emitting region of the backlight to be inspected is exposed and a second light emitting region of the backlight to be inspected, which is a region other than the first light emitting region, is blocked, when the inspection plate is disposed at a second position, a third light emitting region of the backlight to be inspected is exposed and a fourth light emitting region of the backlight to be inspected, which is a region other than the third light emitting region, is blocked, and the third light emitting region is different from the first light emitting region.

Further, the inspection plate includes at least one inspection area through which lights can be transmitted and at least one blocking area that blocks transmission of lights. When the inspection plate is disposed at the first position, a position of the at least one inspection area corresponds to a position of the first light emitting region and the at least one blocking area blocks the second light emitting region, when the inspection plate is disposed at the second position, a position of the at least one inspection area corresponds to a position of the third light emitting region and at least one blocking area blocks the fourth light emitting region.

Further, a first guide rail is disposed on the carrying platform and the inspection plate is disposed on the first guide rail, and the inspection plate is movable along the first guide rail from the first position to the second position.

Further, a first guide rail is disposed on the carrying platform and the inspection plate is disposed on the first guide rail, and the inspection plate is movable along the first guide rail from the first position to the second position.

Further, the backlight inspection equipment further includes a first guide rail, a first stopper structure disposed on one end of the first guide rail, a sliding structure movably disposed on the first guide rail, a second guide rail disposed parallel to the first guide rail, the inspection plate being movably disposed on the sliding structure via the second guide rail, and a second stopper structure disposed on one end of the inspection plate, which is apart from the first stopper. The sliding structure drives the inspection plate to move along the first guide rail in a first direction, the sliding structure stops movement when the sliding structure moves to the first stopper structure, at this time, the inspection plate is positioned at the first position. The inspection plate moves relative to the sliding structure along the second guide rail in the first direction, the inspection plate stops movement when the second stopper structure contacts with one end of the second guide rail, which is apart from the first stopper structure, at this time, the inspection plate is disposed at the second position.

Further, the backlight inspection equipment further includes a third guide rail on which the inspection plate is movably disposed, the third guide rail having a third stopper structure on one end of the third guide rail, and an articulated structure including a first connection member connected with the third guide rail, a second connection member connected with the carrying platform, and a first pivot member connecting the first connection member with the second connection member. The inspection plate rotates to an upper side of the carrying platform via the articulated structure, at this time, the inspection plate is disposed at the first position. The inspection plate moves to the third stopper structure along the third guide rail, at this time, the inspection plate is disposed at the second position.

Further, the inspection plate is rotatably connected with the carrying platform.

Further, the backlight inspection equipment further includes an articulated structure including a third connection member connected with the inspection plate, a fourth connection member connected with the carrying platform, and a second pivot member connecting the third connection member with the fourth connection member, and a rotating structure that rotates the inspection plate to turn over, the rotating structure being disposed between the inspection plate and the third connection member. The articulated structure and the rotating structure work together in order to control a first surface of the inspection plate to face the backlight at the first position and a second surface of the inspection plate, which is opposed to the first surface, to face the backlight at the second position.

Further, the at least one inspection area and the at least one blocking area have same rectangular-shaped structures, and the at least one inspection area and the at least one blocking area are disposed on the inspection plate at intervals.

Further, the inspection plate includes a box structure having an empty sandwich layer, the empty sandwich layer houses a blocking plate. A plurality of through holes are defined on opposed surfaces of the box structure, and the blocking plate is movable in the empty sandwich layer and blocks one of the through holes so that the at least one blocking area is provided, and the remaining through holes that are not blocked by the blocking plate provides the at least one inspection area.

Further, the inspection plate includes a cross-shaped frame structure configured by double-layered sandwich plates and the blocking plate disposed between the double-layered sandwich plates, an inside portion of the cross-shaped frame structure is divided into five portions having equivalent areas, the blocking plate is movable between the double-layered sandwich plates and blocks one of the five portions so that the at least one blocking area is provided, and remaining portions of the five portions provide the at least one inspection area.

Further, a backlight inspection equipment comprises a carrying platform configured to dispose a backlight to be inspected, an inspection plate movably disposed relative to the carrying platform and being able to block a part of a light emitting region of the backlight to be inspected, and an inspection moving unit configured to move the inspection plate to different positions successively. When the inspection plate is disposed at different position, different part of the light emitting region of the backlight to be inspected is exposed.

The present invention provides the following advantages: inspection work difficulty and inspection work intensity is reduced and inspection operational efficiency is improved. After practice, it is proven that defect inspection rate of the backlight having large dimension is effectively improved, and inspection miss is reduced.

DETAILED DESCRIPTION

To make the objects, the technical solutions and the advantages of the present invention more apparent, the following will describe embodiments of the present invention with reference to the drawings. It will be understood that the following embodiments are described only for explaining the present invention, but not to limit the scope of the present invention.

As shown in FIG. 1 to FIG. 7, the present embodiment provides a backlight inspection equipment that includes a carrying platform 1 configured to dispose a backlight to be inspected and an inspection plate 2 movably disposed relative to the carrying platform 1. The inspection plate 2 is movable from a first position to a second position.

When the inspection plate 2 is disposed at the first position, a first light emitting region of the backlight to be inspected is exposed and a second light emitting region, which is a region other than the first light emitting region, is blocked. When the inspection plate 2 is disposed at the second position, a third light emitting region of the backlight to be inspected, which is different from the first light emitting region, is exposed and a fourth light emitting region, which is a region other than the third light emitting region, is blocked by the inspection plate 2.

The different exposed light emitting regions are inspected by moving the inspection plate 2. Thus, inspection work difficulty and inspection work intensity is reduced and inspection operational efficiency is improved. After practice, it is proven that defect inspection rate of the backlight having large dimension is effectively improved, and inspection miss is reduced.

In one exemplary embodiment, the third light emitting region and the second light emitting region may be the same region, and the fourth light emitting region and the first light emitting region may be the same region. As another example, based on actual sizes of the inspection plate 2 and the backlight to be inspected, the third light emitting region and the second light emitting region may be set as different regions, and the fourth light emitting region and the first light emitting region may be set as different regions.

The following will describe a configuration of the backlight inspection equipment according to one exemplary embodiment. In the present embodiment, the third light emitting region 18 and the second light emitting region 16 are the same region, and the fourth light emitting region 17 and the first light emitting region 15 are the same region. When the inspection plate 2 moves from the first position to the second position, an exposed area and a blocked area of the backlight is alternatively switched and an inspection of the entire backlight is performed. With this configuration, visual fatigue of the inspector and inspection miss are reduced.

In the present embodiment, the inspection plate 2 includes at least one inspection area 5 through which lights can be transmitted and at least one blocking area 14 that blocks transmission of lights.

When the inspection plate 2 is disposed at the first position, a position of the at least one inspection area 5 corresponds to a position of the first light emitting region 15 and a position of the at least one blocking area 14 corresponds to a position of the second light emitting region 16. When the inspection plate 2 is disposed at the second position, a position of the at least one inspection area 5 corresponds to a position of the third light emitting region 18 and a position of the at least one blocking area 14 corresponds to a position of the fourth light emitting region 17.

In the present embodiment, a quantity of the at least one inspection area 5, a quantity of the at least one blocking area 14, a shape of the at least one inspection area 5 and a shape of the at least one blocking area 14 may be set according to actual needs. In one exemplary embodiment, each of the at least one inspection area 5 and the at least one blocking area 14 may have the same rectangular shape. The inspection area 5 and the blocking area 14 are arranged on the inspection plate 2 at intervals.

The at least one inspection area 5 and the at least one blocking area 14 may be arranged at intervals on the inspection plate 2 in a plurality of patterns. In the present embodiment, the at least one inspection area 5 and the at least one blocking area 14 are arranged in grid pattern. It should be understood that the grid dimension of the grid pattern is not limited. the at least one inspection area 5 and the at least one blocking area 14 may be arranged based on a movement locus of the inspection plate 2 and a specific portion required to be inspected. Just that an effective partition inspection or inspection to a specific target is able to be performed, the at least one inspection area 5 and the at least one blocking area 14 may be arranged in any pattern.

In one exemplary embodiment, a first guide rail 8 is disposed on the carrying platform 1. The inspection plate 2 is disposed on the first guide rail 8 and the inspection plate 2 moves from the first position to the second position along the first guide rail 8.

Figure 1:
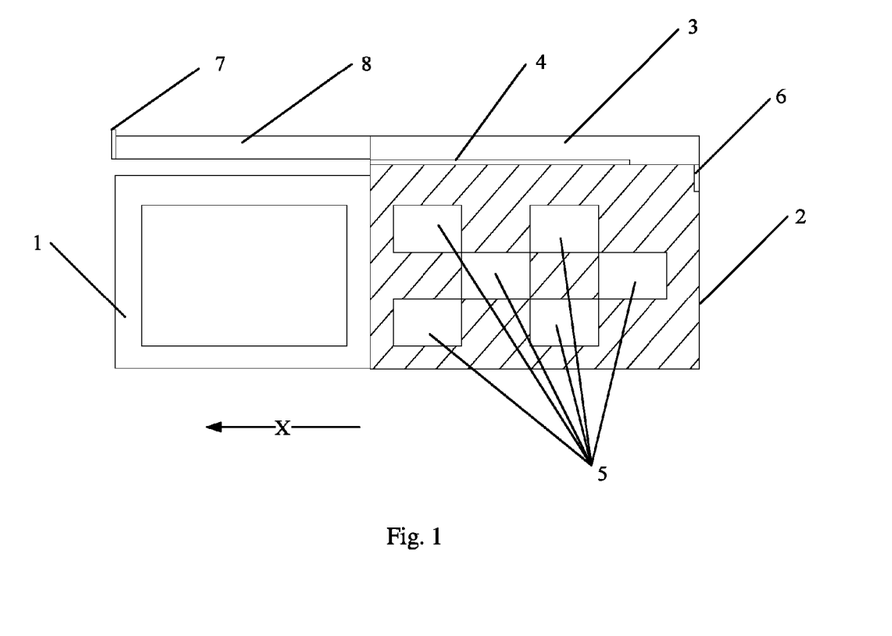
FIG. 1 is a diagram showing a configuration of a backlight inspection equipment according to an embodiment of the present invention.

As shown in FIG. 1, in one exemplary embodiment, the inspection plate 2 includes six inspection areas 5 and the blocking area 14 disposed around the six inspection areas 5.

The backlight inspection equipment further includes the first guide rail 8, a first stopper structure 7 disposed at one end portion of the first guide rail 8, a sliding structure 3 movably disposed on the first guide rail 8, a second guide rail 4 disposed parallel to the first guide rail 8, and a second stopper structure 6 disposed at one end of the inspection plate 2, which is apart from the first stopper structure 7. The inspection plate 2 is movably disposed on the sliding structure 3 via the second guide rail 4.

Figure 2:
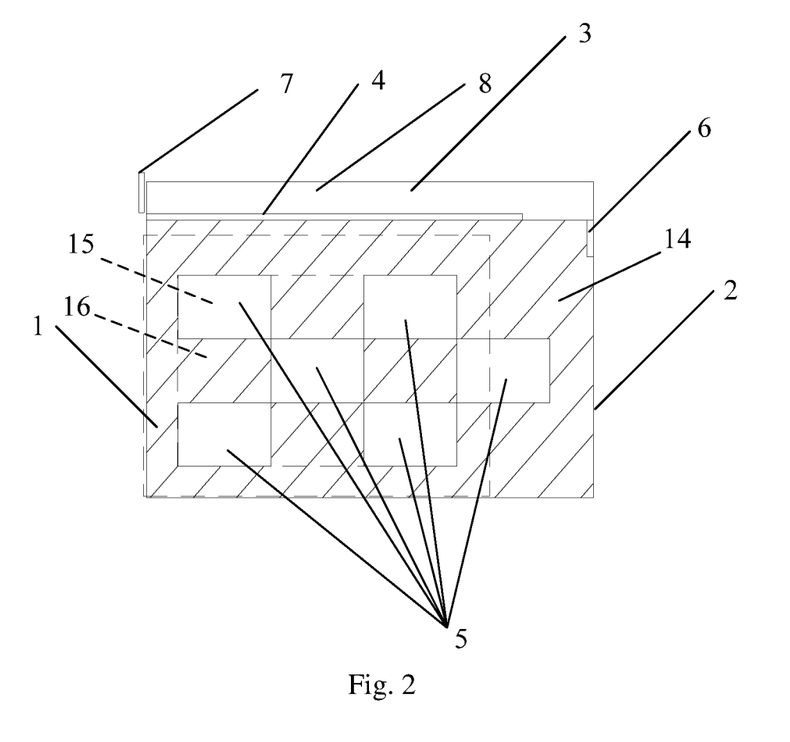
FIG. 2 is a diagram showing an inspection plate when the inspection plate is disposed at a first position.

The sliding structure 3 drives the inspection plate 2 to move in a first direction (X direction in FIG. 1) along the first guide rail 8, and stops movement when the sliding structure 3 moves to the first stopper structure 7. At this time, the inspection plate 2 is disposed at the first position as shown in FIG. 2.

Figure 3:
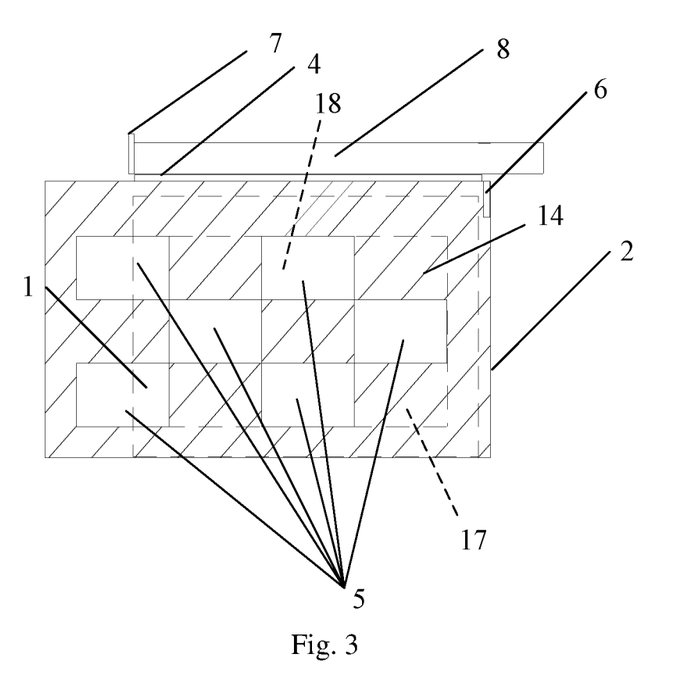
FIG. 3 is a diagram showing the inspection plate when the inspection plate is disposed at a second position.

The inspection plate 2 moves along the second guide rail 4 in the first direction relative to the sliding structure 3, and stops movement when the second stopper structure 6 contacts with one end portion of the second guide rail 4. The end portion of the second guide rail 4 contacts with the second stopper structure 6 is an end portion that is disposed apart from the first stopper structure 7. At this time, the inspection plate 2 is disposed at the second position as shown in FIG. 3.

The inspection plate 2, the second guide rail 4, the sliding structure 3 move together along the first guide rail 8 in a left direction, and stop movement when the sliding structure 3 moves to the first stopper structure 7. At this time, the inspection plate is disposed at the first position, and the first light emitting region 15 corresponding to the five inspection areas 5 disposed on a left side of the inspection plate 2 is exposed and the second light emitting region 16 corresponding to the blocking area 14 of the inspection plate 2 is blocked. The inspector performs inspection to the first light emitting region 15 that corresponds to the five inspection areas 5 disposed on the left side of the inspection plate 2. After the inspection of the first light emitting region 15 is finished, the inspection plate 2 continues to move along the second guide rail 4 in the left direction relative to the sliding structure 3. When the second stopper structure 6 moves to a right end of the second guide rail 4, the inspection plate 2 stops movement. At this time, the inspection plate 2 is disposed at the second position, and the third light emitting region 18 corresponding to the four inspection areas 5 disposed on a right side of the inspection plate 2 is exposed and the fourth light emitting region 17 corresponding to the blocking area 14 of the inspection plate 2 is blocked. That is, the second light emitting region 16, which is blocked by the blocking area 14 when the inspection plate 2 is disposed at the first position, is exposed, and the first light emitting region 15, which is exposed when the inspection plate is disposed at the first position, is blocked by the blocking area 14. The inspector performs inspection to the third light emitting region 18 that corresponds to the four inspection areas 5 disposed on the right side of the inspection plate 2 so that, inspection to the entire backlight is finished.

In the present embodiment, the first stopper structure 7 and the second stopper structure 6 may have different configurations. In one exemplary embodiment, the first stopper structure 7 may be provided by a plate stopper disposed at a left end of the first guide rail 8, and the second stopper structure 6 may be provided by a plate stopper disposed on a right side of the inspection plate 2. But the first stopper structure 7 and the second stopper structure 6 are not limited to this embodiment. As another example, a position sensor and a sensing switch that coordinate with each other can be provided as the stopper structures in order to control the inspection plate 2 to be disposed at the first position or at the second position.

Figure 4:
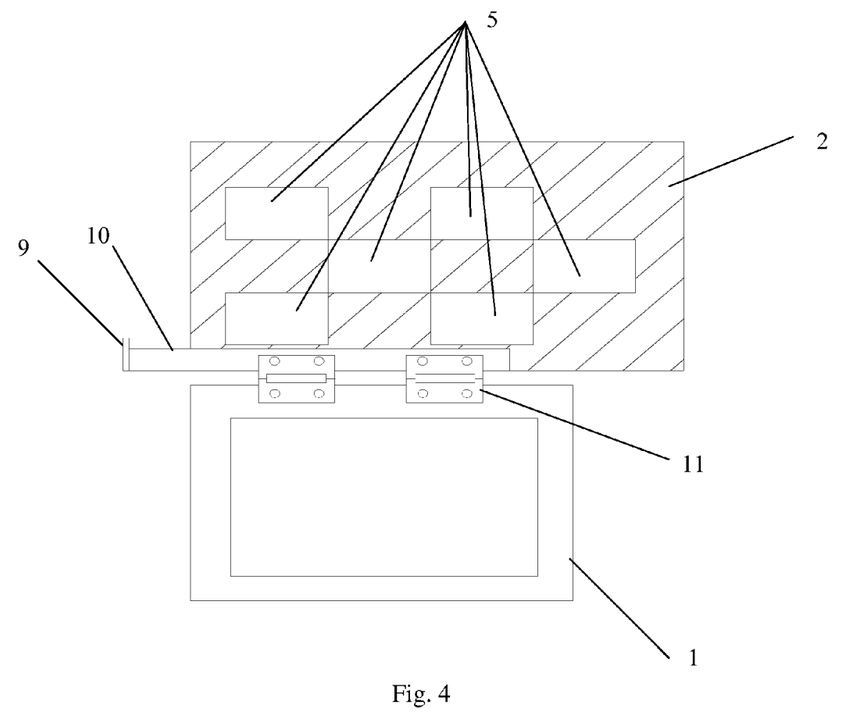
FIG. 4 is a diagram showing a configuration of a backlight inspection equipment according to an embodiment of the present invention.

As shown in FIG. 4, in one exemplary embodiment, the inspection plate 2 includes six inspection areas 5 and the blocking area disposed around the six inspection areas 5.

The backlight inspection equipment may further include a third guide rail 10 on which the inspection plate 2 is movably disposed, an articulated structure 11 including a first connection member, a second connection member, and a first pivot member. A third stopper structure 9 is arranged on one end of the third guide rail 10. The first connection member is connected with the third guide rail 10, the second connection member is connected with the carrying platform 1, and the first pivot member connects the first connection member with the second connection member.

When the inspection plate 2 rotates via the articulated structure 11 to an upper side of the carrying platform 1, the inspection plate 2 is disposed at the first position, When the inspection plate 2 moves to the third stopper structure 9 along the third guide rail 10, the inspection plate 2 is disposed at the second position.

The inspection plate 2 and the third guide rail 10 rotate around the first pivot member. When the inspection plate 2 is disposed at the first position, the inspection plate 2 is disposed at the upper side of the carrying platform 1 and the first light emitting region that corresponds to the five inspection areas 5 disposed on the left side of the inspection plate 2 is exposed and the second light emitting region that corresponds to the blocking area of the inspection plate 2 is blocked. The inspector performs the inspection to the first light emitting region that corresponds to the five inspection areas 5 disposed on the left side of the inspection plate 2. After the inspection of the first light emitting region is finished, the inspection plate 2 moves along the third guide rail 10 in the left direction relative to the carrying platform 1. When the inspection plate 2 moves to the third stopper structure 9, the inspection plate 2 stops movement. At this time, the inspection plate 2 is disposed at the second position, and the third light emitting region that corresponds to the four inspection areas 5 disposed on the right side of the inspection plate 2 is exposed and the fourth light emitting region that corresponds to the blocking area of the inspection plate 2 is blocked. That is, the second light emitting region, which is blocked by the blocking area when the inspection plate 2 is disposed at the first position, is exposed, and the first light emitting region, which is exposed when the inspection plate 2 is disposed at the first position, is blocked by the blocking area. The inspector performs inspection to the third light emitting region that corresponds to the four inspection areas 5 disposed on the right side of the inspection plate 2, so that inspection to the entire backlight is finished.

In the present embodiment, the third stopper structure 9 may have different configurations. In one exemplary embodiment, the third stopper structure 9 may be provided by a plate stopper disposed at an end of the third guide rail 10. But the third stopper structure 9 is not limited to this embodiment. As another example, a position sensor and a sensing switch which coordinate with each other can be provided as the stopper structures in order to control the inspection plate 2 to be disposed at the first position or at the second position.

In one exemplary embodiment, the articulated structure 11 is provided by a hinge. The first connection member is provided by a first hinge plate, the second connection member is provided by a second hinge plate, and the first pivot member is provided by a pivot axis of the hinge. After the rotation of the inspection plate 2, in order to secure the inspection plate 2 is parallel to the backlight unit, which is to be inspected and is disposed on the carrying platform 1, a first groove that houses the first connection member is disposed on the third guide rail 10 and a second groove that houses the second connection member is disposed on the carrying platform 1.

Figure 5:
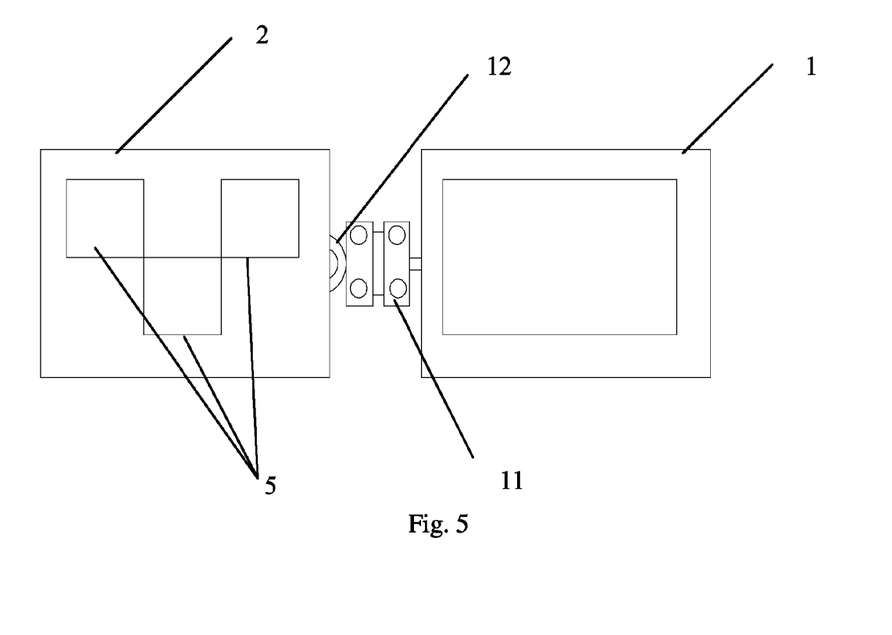
FIG. 5 is a diagram showing a configuration of a backlight inspection equipment according to an embodiment of the present invention.

As shown in FIG. 5, the inspection plate 2 includes three inspection areas 5 arranged in a triangle shape and the blocking area disposed around the three inspection areas 5. The triangle shape means the geometric centers of three inspection areas 5 are positioned at three vertexes of a triangle, respectively.

The backlight inspection equipment further includes an articulated structure 11 and a rotating structure 12 that rotates the inspection plate 2 to turn over. The articulated structure 11 has a third connection member that is connected with the inspection plate 2, a fourth connection member that is connected with the carrying platform 1, and a second pivot member that connects the third connection member with the fourth connection member.

The rotating structure 12 is disposed between the inspection plate 2 and the third connection member.

The articulated structure and the rotating structure work together in order to control a first surface of the inspection plate 2 and a second surface of the inspection plate 2, which is opposed to the first surface, to respectively face the backlight at different times.

In the present embodiment, the first position and the second position are the same position.

The inspection plate 2 rotates around the second pivot member as a rotating axis. When the inspection plate is disposed on the upper side of the carrying platform 1, the inspection plate 2 is disposed at the first position. At this time, the three inspection areas 5 of the inspection plate 2 are arranged in a reversed triangle shape. The first light emitting region corresponding to the three inspection areas 5 of the inspection plate 2 is exposed and the second light emitting region corresponding to the blocking area of the inspection plate 2 is blocked. The inspector performs inspection to the first light emitting region that corresponds to the three inspection areas 5 of the inspection plate 2. After the inspection to the first light emitting region is finished, the inspection plate 2 rotates in an opposite direction by a predetermined angle. The predetermined angle is set to at least 90 degrees. Then, the inspection plate 2 rotates by 180 degrees via the rotating structure 12 and turns over. After the rotation, the three inspection areas 5 disposed on an upper side of the inspection plate 2 are arranged in a triangle shape. The inspection plate 2 rotates around the second pivot member as a rotating axis to the upper side of the carrying platform 1. At this time, the inspection plate 2 is disposed at the second position, and the third light emitting region corresponding to the three inspection areas 5 of the inspection plate 2 is exposed and the fourth light emitting region corresponding to the blocking area of the inspection plate 2 is blocked. That is, the second light emitting region, which is blocked by the blocking area when the inspection plate 2 is disposed at the first position, is exposed, and the first light emitting region, which is exposed when the inspection plate 2 is disposed at the first position, is blocked by the blocking area. The inspector performs inspection to the third light emitting region that corresponds to the three inspection areas 5 of the inspection plate 2 so that inspection to the entire backlight is finished.

In the present embodiment, the articulated structure 11 is provided by a hinge. The third connection member is provided by a first hinge plate, the fourth connection member is provided by a second hinge plate, and the second pivot member is provided by a pivot axis of the hinge.

In the present embodiment, the rotating structure 12 includes a rolling ball disposed between the inspection plate 2 and the first connection member, but not limited to the rolling ball.

In another embodiment, the inspection plate 2 includes a box structure having an empty sandwich layer. The empty sandwich layer houses a blocking plate 13, and multiple through holes are defined on opposed surfaces of the box structure. The blocking plate 13 is movable in the empty sandwich layer in order to block one of the through holes so that the blocking area is formed, and the through hole that is not blocked forms the inspection area 5.

Figure 6:
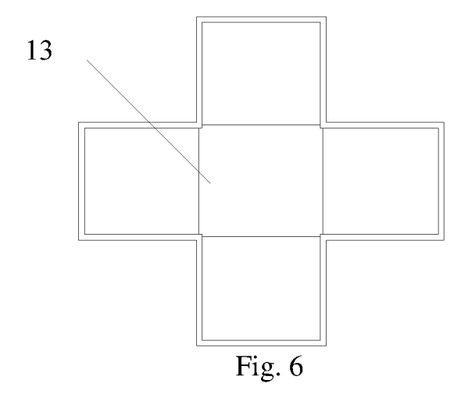
FIG. 6 is a diagram showing a configuration of a backlight inspection equipment according to an embodiment of the present invention.
Figure 7:
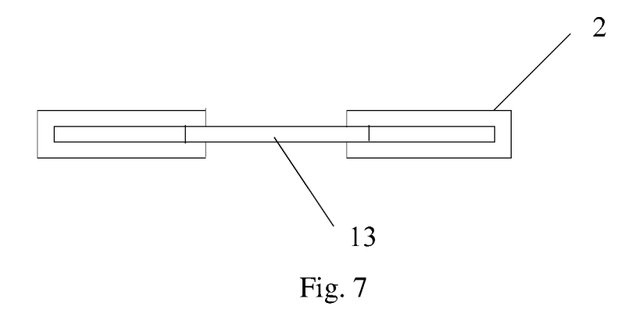
FIG. 7 is a diagram showing a side view of the backlight inspection equipment shown in FIG. 6.

As shown in FIG. 6 and FIG. 7, the inspection plate 2 includes a cross-shaped frame structure configured by double-layered sandwich plates and the blocking plate 13 disposed between the double-layered sandwich plates. An inside portion of the cross-shaped frame structure is divided into five portions having equivalent areas. The blocking plate 13 is movable between the double-layered sandwich plates in order to block one of the five portions so that the blocking area is formed and remaining portions of the five portions form the inspection areas 5.

The blocking plate 13 is disposed at a middle portion of the cross-shaped frame. That is, the second light emitting region corresponding to the middle portion of the cross-shaped frame is blocked by the blocking plate 13 and the first emitting region corresponding to the four inspection areas 5 disposed at the periphery portion of the cross-shaped frame are exposed. At this time, the inspection plate is disposed at the first position. The inspector performs inspection to the first light emitting region that corresponds to the four inspection areas 5 disposed at the periphery portion of the cross-shaped frame. After the inspection is finished, the blocking plate 13 moves in one of upward direction, downward direction, left direction or right direction so that one of the periphery portions of the cross-shaped frame to provide the blocking area, that is, to provide the blocked fourth light emitting region (fourth light emitting region is provided by a part of the first light emitting region), and the third light emitting region corresponding to the middle portion of the cross-shaped frame is exposed. That is, the second light emitting region, which is blocked when the inspection plate 2 is disposed at the first position, is exposed. At this time, the inspection plate 2 is disposed at the second position. The inspector performs inspection to the third light emitting region so that inspection to the entire backlight is finished.

With the above-described cross-shaped frame structure, important inspection target areas can be selectively inspected and less important areas can be blocked, and inspection efficiency can be improved.

In the present embodiment, a shape of the inspection plate 2, a quantity of the through holes and shapes of the through holes can be set without limitation under a condition that the entire backlight can be inspected.

In the above, the backlight inspection equipment is described, wherein the inspection is performed to different areas of the backlight by positioning the inspection plate at the first position and the second position. But it is not limited to the first position and the second position. For example, the position of the inspection plate may be changed among three or more than three positions. Specifically speaking, the inspection plate may move from the first position to the Nth position by an inspection plate moving unit in order to expose different light emitting area of the backlight required to be inspected at different position. The inspection plate moving unit may move the inspection plate by a stepping motor or the like.

It should be noted that, in the present embodiment, directional descriptions, such as, "upward", "downward", "left", "right" are the directions with reference to the drawings, but not limit the scope of the backlight inspection equipment according to the present embodiment.

While the invention has been described with reference to preferred embodiments thereof, it should be noted that for a person skilled in the art, without departing from a spirit of the present invention, further improvements and modifications can be made, and these improvements and modifications are also included in the scope of the present invention.

What is claimed is:

1. A backlight inspection equipment comprising:
   a carrying platform configured to position a backlight for inspection; and
   an inspection plate movably disposed relative to the carrying platform while the backlight is positioned on the carrying platform, and disposed above the backlight while the backlight is positioned on the carrying platform, the inspection plate being movable between a first position and a second position relative to the carrying platform, the inspection plate including at least one inspection area and at least one blocking area, the at least one inspection area is a part of the inspection plate through which light from the backlight is transmittable through the inspection plate, and the at least one blocking area is a part of the inspection plate that blocks light from the backlight from being transmitted through the inspection plate;
   wherein, a first light emitting region of the backlight is exposed through the at least one inspection area of the inspection plate and a second light emitting region of the backlight is blocked by the at least one blocking region of the inspection plate when the inspection plate is in the first position;
   wherein, a third light emitting region of the backlight is exposed through the at least one inspection area of the inspection plate and a fourth light emitting region of the backlight is blocked by the at least one blocking area of the inspection plate when the inspection plate is in the second position;
   wherein the first light emitting region is different from the second light emitting region, the second light emitting region is different from the fourth light emitting region, and the third light emitting region is different from the first light emitting region and the fourth light emitting region.

2. The backlight inspection equipment according to claim 1, wherein:
   when the inspection plate is disposed at the first position, a position of the at least one inspection area corresponds to a position of the first light emitting region and the at least one blocking area blocks the second light emitting region, when the inspection plate is disposed at the second position, a position of the at least one inspection area corresponds to a position of the third light emitting region and the at least one blocking area blocks the fourth light emitting region.

3. The backlight inspection equipment according to claim 2, wherein
   a first guide rail is disposed on the carrying platform and the inspection plate is disposed on the first guide rail, and the inspection plate is movable along the first guide rail from the first position to the second position.

4. The backlight inspection equipment according to claim 2, further comprising:
   a first guide rail;
   a first stopper structure disposed on one end of the first guide rail;
   a sliding structure movably disposed on the first guide rail;
   a second guide rail disposed parallel to the first guide rail, the inspection plate being movably disposed on the sliding structure via the second guide rail; and
   a second stopper structure disposed on one end of the inspection plate, which is apart from the first stopper, wherein:
   the sliding structure drives the inspection plate to move along the first guide rail in a first direction, the sliding structure stops movement when the sliding structure moves to the first stopper structure, at this time, the inspection plate is positioned at the first position; and
   the inspection plate moves relative to the sliding structure along the second guide rail in the first direction, the inspection plate stops movement when the second stopper structure contacts with one end of the second guide rail, which is apart from the first stopper structure, at this time, the inspection plate is disposed at the second position.

5. The backlight inspection equipment according to claim 2, further comprising:
   a third guide rail on which the inspection plate is movably disposed, the third guide rail having a third stopper structure on one end of the third guide rail; and
   an articulated structure comprising a first connection member connected with the third guide rail, a second connection member connected with the carrying platform, and a first pivot member connecting the first connection member with the second connection member, wherein:

the inspection plate rotates to an upper side of the carrying platform via the articulated structure, at this time, the inspection plate is disposed at the first position; and the inspection plate moves to the third stopper structure along the third guide rail, at this time, the inspection plate is disposed at the second position.

6. The backlight inspection equipment according to claim 2, wherein the inspection plate is rotatably connected with the carrying platform.

7. The backlight inspection equipment according to claim 6, further comprising:

an articulated structure comprising a third connection member connected with the inspection plate, a fourth connection member connected with the carrying platform, and a second pivot member connecting the third connection member with the fourth connection member; and a rotating structure that rotates the inspection plate to turn over, the rotating structure being disposed between the inspection plate and the third connection member, wherein the articulated structure and the rotating structure work together in order to control a first surface of the inspection plate to face the backlight at the first position and a second surface of the inspection plate, which is opposed to the first surface, to face the backlight at the second position.

8. The backlight inspection equipment according to claim 2, wherein the at least one inspection area and the at least one blocking area have same rectangular-shaped structures, and the at least one inspection area and the at least one blocking area are disposed on the inspection plate at intervals.

9. The backlight inspection equipment according to claim 3, wherein the at least one inspection area and the at least one blocking area have same rectangular-shaped structures, and the at least one inspection area and the at least one blocking area are disposed on the inspection plate at intervals.

10. The backlight inspection equipment according to claim 4, wherein the at least one inspection area and the at least one blocking area have same rectangular-shaped structures, and the at least one inspection area and the at least one blocking area are disposed on the inspection plate at intervals.

11. The backlight inspection equipment according to claim 5, wherein the at least one inspection area and the at least one blocking area have same rectangular-shaped structures, and the at least one inspection area and the at least one blocking area are disposed on the inspection plate at intervals.

12. The backlight inspection equipment according to claim 6, wherein the at least one inspection area and the at least one blocking area have same rectangular-shaped structures, and the at least one inspection area and the at least one blocking area are disposed on the inspection plate at intervals.

13. The backlight inspection equipment according to claim 7, wherein the at least one inspection area and the at least one blocking area have same rectangular-shaped structures, and the at least one inspection area and the at least one blocking area are disposed on the inspection plate at intervals.

14. The backlight inspection equipment according to claim 2, wherein the inspection plate comprises:

a box structure having an empty sandwich layer, the empty sandwich layer houses at least one blocking plate, multiple through holes being defined on opposed surfaces of the box structure, the blocking plate being movable in the empty sandwich layer and blocking at least one of the through holes so that the at least one blocking area is provided, and the remaining through holes that are not blocked by the blocking plate providing the at least one inspection area.

15. The backlight inspection equipment according to claim 14, wherein the inspection plate comprises a cross-shaped frame structure configured by double-layered sandwich plates and the blocking plate disposed between the double-layered sandwich plates, an inside portion of the cross-shaped frame structure is divided into five portions having equivalent areas, the blocking plate is movable between the double-layered sandwich plates and blocks one of the five portions so that the blocking area is provided, and remaining portions of the five portions provide the inspection area.

16. A backlight inspection equipment comprising:

a carrying platform configured to position a backlight for inspection;

an inspection plate movably disposed relative to the carrying platform while the backlight is positioned on the carrying platform and being able to cover a part of a light emitting region of the backlight unit while the backlight is positioned on the carrying platform, the inspection plate including at least one inspection area and at least one blocking area, the at least one inspection area is a part of the inspection plate through which light from the backlight is transmittable through the inspection plate, and the at least one blocking area is a part of the inspection plate that blocks light from the backlight from being transmitted through the inspection plate; and an inspection plate moving unit configured to move the inspection plate to different positions successively while the backlight is positioned on the carrying platform, when the inspection plate is disposed at different positions, different parts of the light emitting region of the backlight are exposed through the at least one inspection area of the inspection plate and other parts of the light emitting region of the backlight are blocked by the at least one blocking area the inspection plate.

17. The backlight inspection equipment according to claim 16, wherein the inspection plate moving unit comprises a stepping motor.

* * * * *